(12) United States Patent
Burton

(10) Patent No.: US 10,286,192 B2
(45) Date of Patent: May 14, 2019

(54) METHODS FOR MAKING A BALLOON CATHETER AND FOR PRODUCING AN INVENTORY OF BALLOON CATHETERS

(71) Applicant: Cook Medical Technologies LLC, Bloomington, IN (US)

(72) Inventor: David Burton, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 721 days.

(21) Appl. No.: 14/728,235

(22) Filed: Jun. 2, 2015

(65) Prior Publication Data

US 2016/0022967 A1 Jan. 28, 2016

Related U.S. Application Data

(60) Provisional application No. 62/029,013, filed on Jul. 25, 2014.

(51) Int. Cl.
| | |
|---|---|
| *B29C 49/04* | (2006.01) |
| *A61M 25/10* | (2013.01) |
| *B29C 49/48* | (2006.01) |
| *B29K 105/00* | (2006.01) |
| *B29L 31/00* | (2006.01) |
| *B29C 33/30* | (2006.01) |
| *B29C 49/14* | (2006.01) |

(52) U.S. Cl.
CPC .... *A61M 25/1029* (2013.01); *A61M 25/1038* (2013.01); *B29C 49/48* (2013.01); *B29C 33/308* (2013.01); *B29C 49/04* (2013.01); *B29C 49/14* (2013.01); *B29C 2049/481* (2013.01); *B29C 2049/4858* (2013.01); *B29C 2049/4894* (2013.01); *B29K 2105/258* (2013.01); *B29L 2031/7543* (2013.01)

(58) Field of Classification Search
CPC ............................................... B29C 2049/481
See application file for complete search history.

(56) References Cited

U.S. PATENT DOCUMENTS

| | | | |
|---|---|---|---|
| 3,380,121 A | 4/1968 | Chittenden et al. | |
| 4,789,129 A | 12/1988 | Sista | |
| 4,815,960 A | 3/1989 | Rudolph | |
| 5,731,013 A | 3/1998 | Vandersanden | |
| 6,561,788 B1 | 5/2003 | Gaudoin | |
| 6,835,059 B2 | 12/2004 | Skinner et al. | |
| 7,060,218 B2 | 6/2006 | Skinner et al. | |
| 7,892,201 B1 | 2/2011 | Laguna et al. | |
| 8,585,959 B2 | 11/2013 | Burton | |
| 2002/0125617 A1 | 9/2002 | Skinner et al. | |
| 2009/0292347 A1* | 11/2009 | Asmus | A61F 2/958 623/1.11 |

FOREIGN PATENT DOCUMENTS

JP 200211377 4/2002

* cited by examiner

*Primary Examiner* — Ryan M Ochylski
(74) *Attorney, Agent, or Firm* — Liell & McNeil

(57) ABSTRACT

Making a balloon catheter includes increasing a temperature of material forming an elongate body positioned within a cavity in an adjustable molding iris, and increasing a fluid pressure within a lumen extending through the elongate body. A segment of the elongate body is plastically deformed in response to the increased fluid pressure, and limited in outward expansion via contacting movable blade members forming the adjustable molding iris.

3 Claims, 5 Drawing Sheets

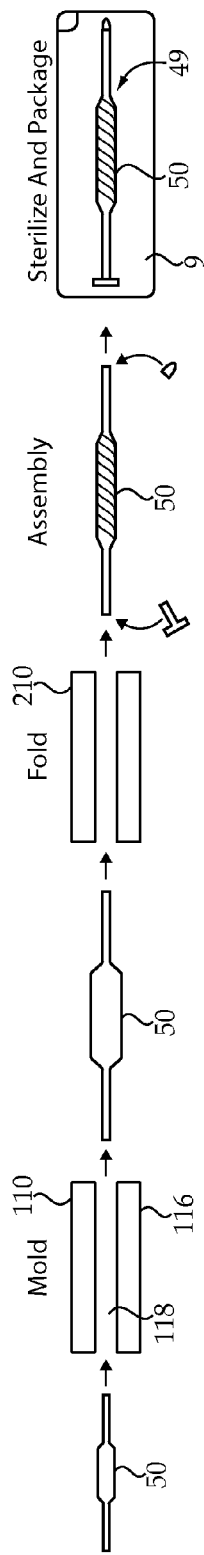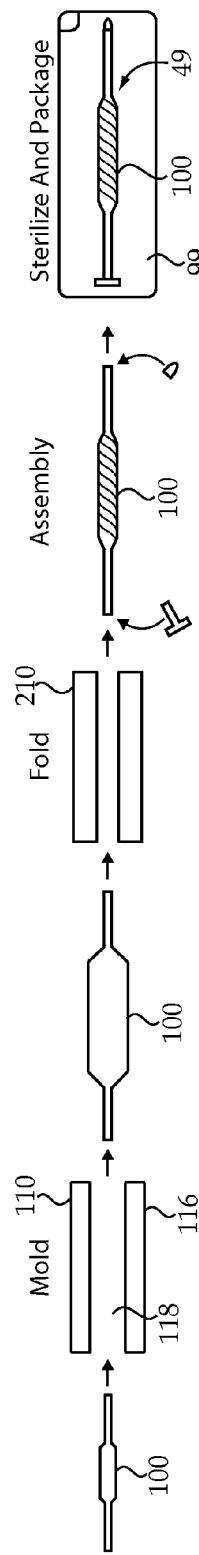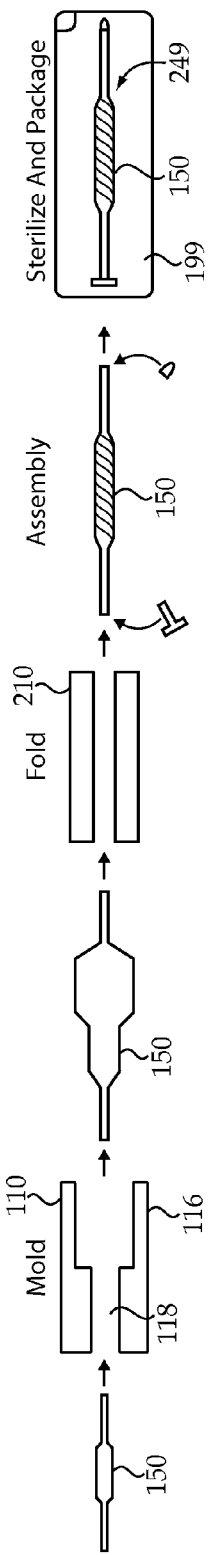

METHODS FOR MAKING A BALLOON CATHETER AND FOR PRODUCING AN INVENTORY OF BALLOON CATHETERS

TECHNICAL FIELD

The present disclosure relates generally to techniques for making balloon catheters, and more particularly to blow molding balloon catheters in an adjustable molding iris.

BACKGROUND

A great many different techniques and apparatuses for making medical devices have been proposed over the years. In the case of balloons for angioplasty and other interventional treatments, production tends to be relatively labor intensive. Current balloon molds are typically fixed in size, and therefore specialized for molding a balloon of a particular configuration. In a typical setup, a tubular die is provided that has a center piece and two end caps. An elongate tubular body of starting material for the balloon to be formed is positioned in the center piece of the die, and the end caps for forming a cone and neck of the balloon are coupled to the center piece. The die is then typically positioned within a fixture, and pressurized air is supplied to the elongate tubular body to blow mold a balloon therein. Heat applied to the exterior of the die softens material of the elongate body to facilitate its plastic deformation during blow molding. Once formed, the balloon can be removed from the die for further processing. While this general technique and apparatus has worked well for many years, it is not without drawbacks, notably the requirement to use a dedicated die for each balloon configuration to be molded.

SUMMARY

In one aspect, making a balloon catheter includes advancing an elongate body into a cavity defined by a plurality of movable blade members forming an adjustable molding iris, and increasing a temperature of material forming the elongate body so as to soften the material, once positioned within the cavity. The method further includes increasing a fluid pressure within a lumen extending longitudinally through the elongate body, and plastically deforming a segment of the elongate body formed by the softened material, in response to the increased fluid pressure such that a tubular wall defining the lumen within the segment expands outwardly about a longitudinal axis of the elongate body. The method further includes limiting the outward expansion via contacting the expanded tubular wall with the plurality of movable blade members while the molding iris is held in a fixed state, such that upon hardening of the material the tubular wall forms an inflatable balloon in fluid communication with the lumen in an adjoining segment of the tubular body.

In another aspect, a method of producing an inventory of balloon catheters includes advancing a first elongate body into a cavity defined by a plurality of movable blade members forming an adjustable molding iris, and blow molding a first balloon in the first elongate body while the molding iris is held in a first state determining a configuration of the first balloon. The method further includes advancing a second elongate body into the cavity in place of the first elongate body, and blow molding a balloon in the second elongate body while the molding iris held in a second state determining a configuration of the second balloon. The method still further includes populating the inventory with a first balloon catheter and a second balloon catheter assembled from the first and second elongate bodies, respectively.

In still another aspect, a method of making a balloon catheter includes moving a plurality of blade members defining a cavity in a molding iris so as to adjust the molding iris from a first state to a second state, advancing an elongate body into the cavity, and increasing a temperature of material forming the elongate body so as to soften the material, once positioned within the cavity. The method further includes increasing a fluid pressure within a lumen extending longitudinally through the elongate body, and plastically deforming a segment of the elongate body formed by the softened material, in response to the increased fluid pressure, so as to outwardly expand the segment. The method still further includes limiting the outward expansion via contacting the segment with the plurality of movable blade members, such that upon hardening of the material the segment forms an inflatable balloon having a configuration determined by the second state of the molding iris and in fluid communication with the lumen in an adjoining segment of the tubular body.

BRIEF DESCRIPTION OF THE DRAWINGS

FIG. 7a is a pictorial process flow diagram, according to one embodiment;

FIG. 7b is a pictorial process flow diagram, according to one embodiment;

FIG. 7c is yet another pictorial process flow diagram, according to one embodiment.

DETAILED DESCRIPTION

Figure 1:
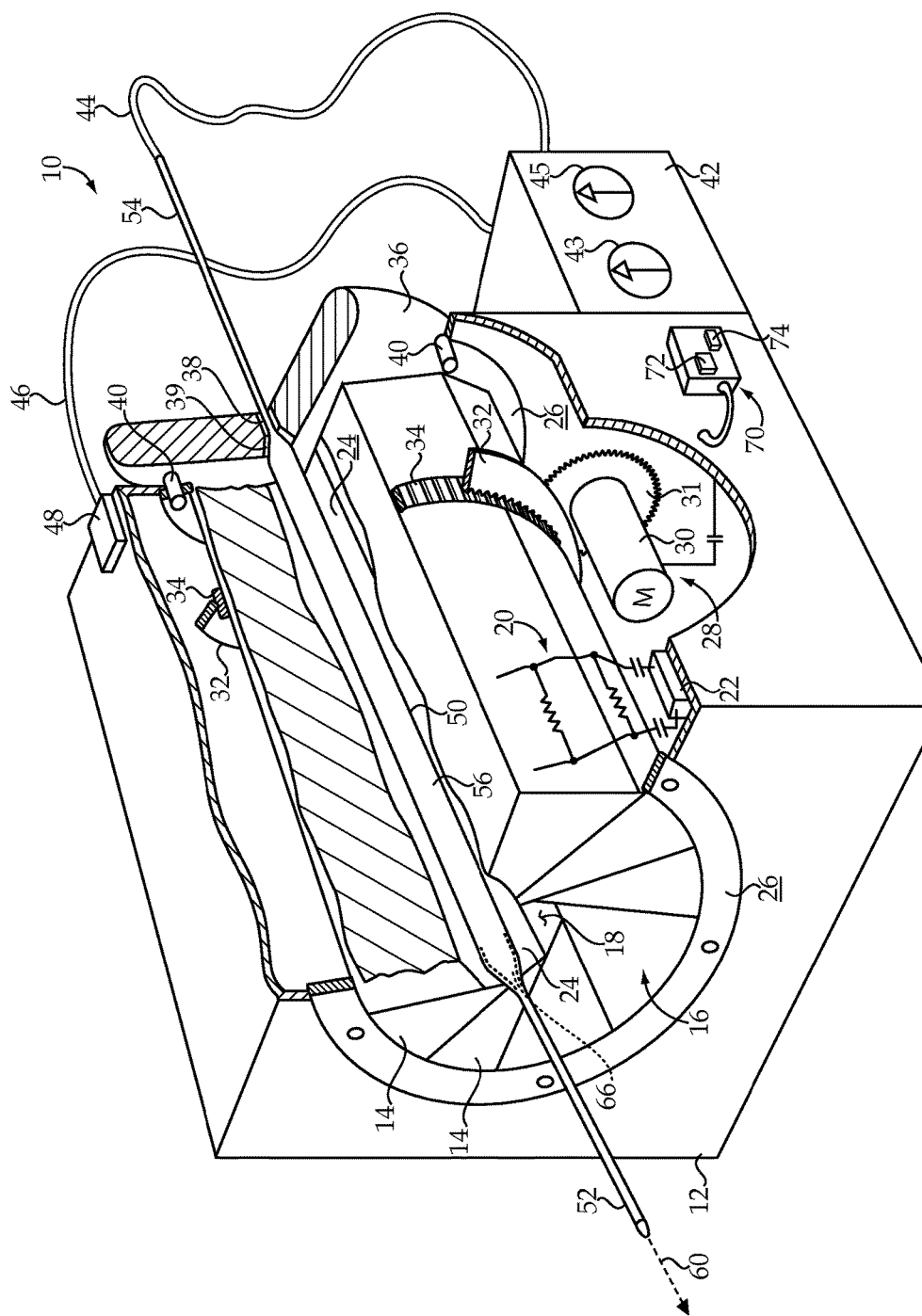
FIG. 1 is a diagrammatic view, in cutaway and partially sectioned in two section planes, of a molding system according to one embodiment.

Referring to FIG. 1, there is shown a molding system 10, according to one embodiment, and including a housing 12 and a plurality of movable blade members 14 defining a cavity 18, and forming an adjustable molding iris 16. An elongate tubular body 50 to be used in forming a balloon catheter has been advanced into cavity 18. Elongate body 50 includes an end segment 52, a second end segment 54, and a middle segment 56 extending between and adjoining end segments 52 and 54. It can be noted that middle segment 56 is larger in diameter than either of end segments 52 and 54. Body 50 may be formed into the configuration shown in FIG. 1 by drawing down each of end segments 52 and 54 under heating and tension to leave middle segment 56 in the form it might have from extruding a single tubular piece. The starting piece might thus have first and second reduced diameter end segments extending from opposite ends of a larger diameter middle segment, although the present disclosure is not thereby limited. When advanced into molding iris 16, the reduced diameter segments will extend from opposite ends of the molding iris approximately as shown. Elongate body 50 also has a tubular wall 58 defining a longitudinally extending lumen 66 through each of segments 52, 54 and 56. Lumen 66 further defines a longitudinal axis 60. As will be further apparent from the following description, system 10 may be uniquely configured for blow molding elongate body 50, and other suitable elongate bodies, for forming balloon catheters. In contrast to prior techniques, molding iris 16 serves as an adjustable size molding die enabling not only flexibility in molding different size balloon catheters, but also in the techniques applied to mold individual balloon catheters, as further discussed herein.

To this end, system 10 may be configured to increase a temperature of material forming elongate body 50 so as to soften the material, once positioned within the cavity. In a practical implementation strategy, system 10 is equipped with a plurality of resistance heaters 20 attached to or positioned in proximity to movable blade members 14, and connected with an electrical power supply 22. Heated air, heated liquid, radiant heating elements, or any other suitable strategy for increasing a temperature of movable blade members 14 so as to heat material of an elongate body contacting or in proximity to movable blade members 14 could be used. Cavity 18 may itself be defined by surfaces 24 of movable blade members 14, which are movable during the adjustment of iris 16. It can be seen from FIG. 1 that movable blade members 14 have the general form of an elongated wedge shape, being generally triangular in cross section. In other instances, movable blade members 14 might have a curved shape, such that surfaces 24 are arcuate rather than planar as shown. It can also be seen that each of movable blade members 14 is positioned in contact with two adjacent movable blade members 14, and slides in contact with the adjacent two blade members during adjustment of iris 16. Also in a practical implementation strategy, blade members 14 may be synchronously pivoted or otherwise synchronously moved to adjust the size of iris 16. Movable blade members 14 may also be mounted within housing 12 via any suitable means, with housing end rings 26 positioned at opposite ends of iris 16. Blade members 14 might be positioned for translational movement in addition to pivoting movement in certain instances.

The adjustment of movable blade members 14 may further be carried out by way of an actuating mechanism 28 that includes a motor 30, such as a servo motor, and a drive gear 31 coupled between motor 30 and a gear ring 32 that extends circumferentially about movable blade members 14. Movable blade members 14 may be coupled with one or more driven elements 34 in mesh with gear ring 32 such that rotation of gear ring 32, in directions shown approximately by way of the curved arrow on gear ring 32 in FIG. 1, adjusts a size of iris 16. Actuating mechanism 28 may rotatably support blade members 14 within housing 12, and while only one gear ring is shown in FIG. 1 multiple gear rings might be used and positioned at different axial locations about movable blade members 14. Individual electric motors coupled with blade members 14 might be used, pneumatic or hydraulic actuators, or any other suitable mechanical contrivance.

Also shown in FIG. 1 is an end support 36 positioned at one end of iris 16. In a practical implementation strategy, end support 36 is one of two end supports, the other of which is positioned at an opposite axial end of iris 16 but omitted from the illustration in FIG. 1. Reduced diameter segments 52 and 54 will typically each be positioned within one of the end supports during blow molding. End support 36 can be coupled to housing end ring 26, for instance via pins 40. It can be seen that elongate body 50 extends through end support 36, and in particular passes through an aperture 38 formed therein and including a tapered surface 39, having a conical shape and tapered such that surface 39 enlarges in the direction of iris 16. As will be further apparent from the following description, the internal shape of end support 36 enables plastic deformation of tubular wall 58 to form a tapered shape via contact with inner surface 39 that limits outward expansion of tubular wall 58. End support 36 and the opposite end support not shown, will typically be removable from housing 12 to facilitate advancing elongate body into and out of cavity 18.

System 10 is further configured to increase a fluid pressure, such as a gaseous fluid pressure, within lumen 66 so as to blow mold a balloon in elongate body 50. To this end, system 10 further includes a fluid supply 42, which might or might not be coupled to housing 12, and including at least one pump or compressor 43, and potentially an additional pump or compressor 45, with a first fluid line 44 connected to pump 43, and a second fluid line 46 connected to pump 45. A cooling air inlet 48 is formed in or coupled to housing 12, so as to enable cooling air or another fluid to be passed through line 46 and into housing 12. As shown in FIG. 1, line 44 fluidly connects with elongate body 50, for increasing a fluid pressure within lumen 66 to blow mold a balloon in elongate body 50. The increased fluid pressure will tend to plastically deform segment 56, formed by material in elongate body 50 softened via the increase in temperature. Tubular wall 58 expands outwardly in response to the increased fluid pressure about longitudinal axis 60. Outward expansion of tubular wall 58 is limited via contacting the expanded tubular wall 58 with movable blade members 14 while molding iris 16 is held in a fixed state, such that upon hardening of the material tubular wall 58 forms an inflatable balloon in fluid communication with lumen 66 in an adjoining segment of tubular body 50, such as segment 52 or segment 54, or both. Lumen 66 may be blocked within segment 52, to enable the increase of fluid pressure within segment 56. The fluid used in blow molding, both for the plastic deformation and for cooling, may be air, but in other embodiments could be a different gas or even a liquid. Also shown in FIG. 1 are operator controls 70, mounted to housing 12 and including a first button 72 and a second button 74, which could be used for a variety of purposes, but in one practical implementation strategy will be used for controlling motor 30 and fluid supply 42, respectively. Additional switches, buttons, a GUI, or any other suitable input devices could be provided.

Figure 2:
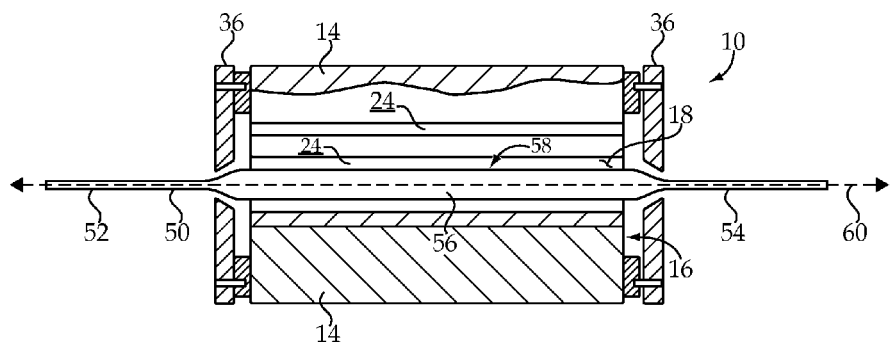
FIG. 2 is a sectioned side diagrammatic view of a portion of the molding system of FIG. 1 in a first state.
Figure 3:
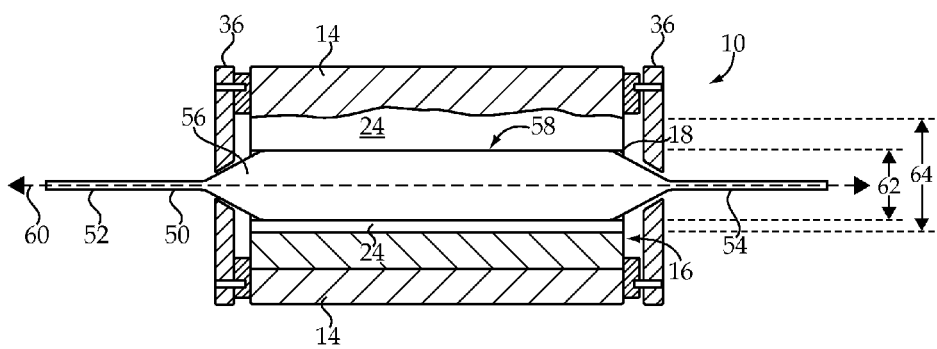
FIG. 3 is a sectioned side diagrammatic view of a portion of the molding system of FIG. 1, in a second state.

Referring also now to FIG. 2, there is shown a sectioned view through system 10 and elongate body 50 where iris 16 is held in a fixed state and elongate body 50 has been advanced into cavity 18. Positioning iris 16 in a fixed state prior to supplying the pressurized air into lumen 66 predetermines a configuration of the balloon to be formed. At the process stage shown in FIG. 2, the temperature of material forming elongate body 50 may be increased so as to soften the material, and subsequently fluid pressure within lumen 66 may be increased to plastically deform segment 56 in the manner described herein. Referring also now to FIG. 3, there is shown a similar sectioned view where middle segment 56 has been expanded outwardly and tubular wall 58 has contacted blade members 14 so as to limit the outward expansion. In FIG. 3, an approximate first expanded diameter 62, corresponding to the actual expanded diameter of segment 56 is shown. Those skilled in the art will appreciate that iris 16 has been held in a fixed state to determine the configuration, including the diameter, of expanded tubular segment 56. A second expanded diameter 64 is shown in FIG. 3, and corresponds to a diameter that might be obtained where iris 16 is held in a different fixed state during the blow molding process. As also further discussed herein, embodiments are contemplated where iris 16 is adjusted during the blow molding process to various ends.

Figure 4:
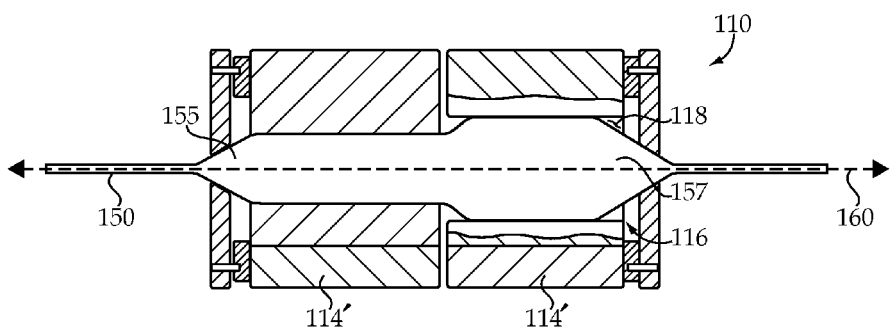
FIG. 4 is a sectioned side diagrammatic view of a molding system, according to another embodiment.

Referring now to FIG. 4, there is shown a molding system 110 according to another embodiment, and including an adjustable molding iris 118 formed by a plurality of movable blade members 114 and 114'. Movable blade members 114 and 114' define a cavity 116 having an elongate body 150 positioned therein, and in particular including a first segment 155 positioned within a first portion of iris 118 formed by blade members 114, and a second segment 157 positioned within a second portion of iris 118 formed by blade members 114'. It will be noted that segments 155 and 157, which may be coaxial about a longitudinal axis 160 but might not be in other embodiments, have different diameters. In the illustrated embodiment, movable blade members 114 and movable blade members 114' are independently adjustable to enable balloons having non-uniform diameters to be molded. Since cavity 118 has a first internal diameter where defined by blade members 114, and a second, larger internal diameter where defined by blade members 114', the balloon formed by blow molding elongate body 150 can have the different shapes shown.

INDUSTRIAL APPLICABILITY

Figure 5:
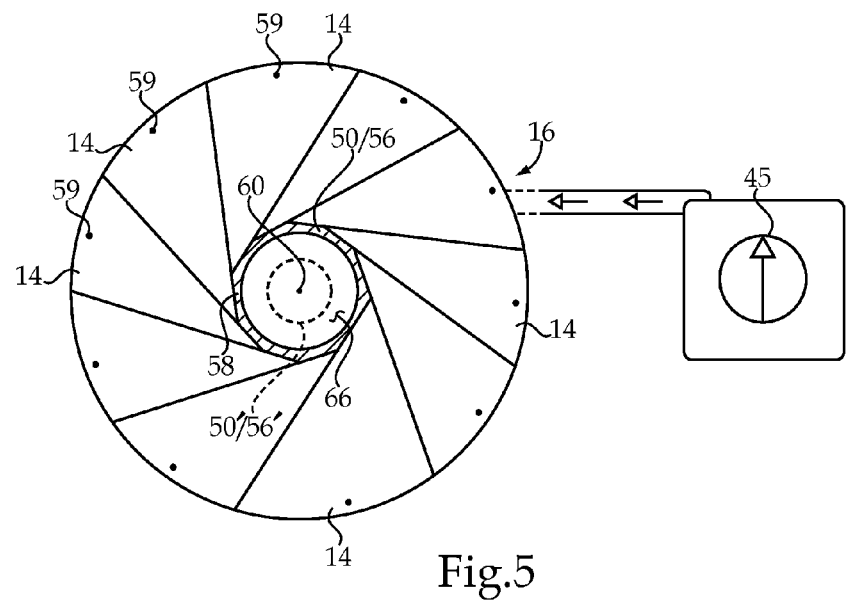
FIG. 5 is an axial view, partially sectioned, through a portion of a molding system, at one stage of a blow molding procedure.

Referring now to FIG. 5, there is shown an axial sectioned view of elongate body 50, through middle segment 56, and illustrated as it might appear where movable blade members 14 have been held in a fixed configuration, and pump 45 has been operated in fluid supply 42 to increase fluid pressure within lumen 66. Tubular wall 58 has expanded outwardly so that its outward expansion is limited via contact with movable blade members 14. As discussed above, material forming elongate body 50 may be increased in temperature and softened via convection of heat from surfaces of blade members 14 and/or via some other heating strategy. Once segment 56 has been plastically deformed to the shape generally desired for a balloon, it may be desirable to hasten hardening of material in elongate body 50 via cooling fluid such as air passed between movable blade members 14, and about tubular wall 58.

Figure 6:
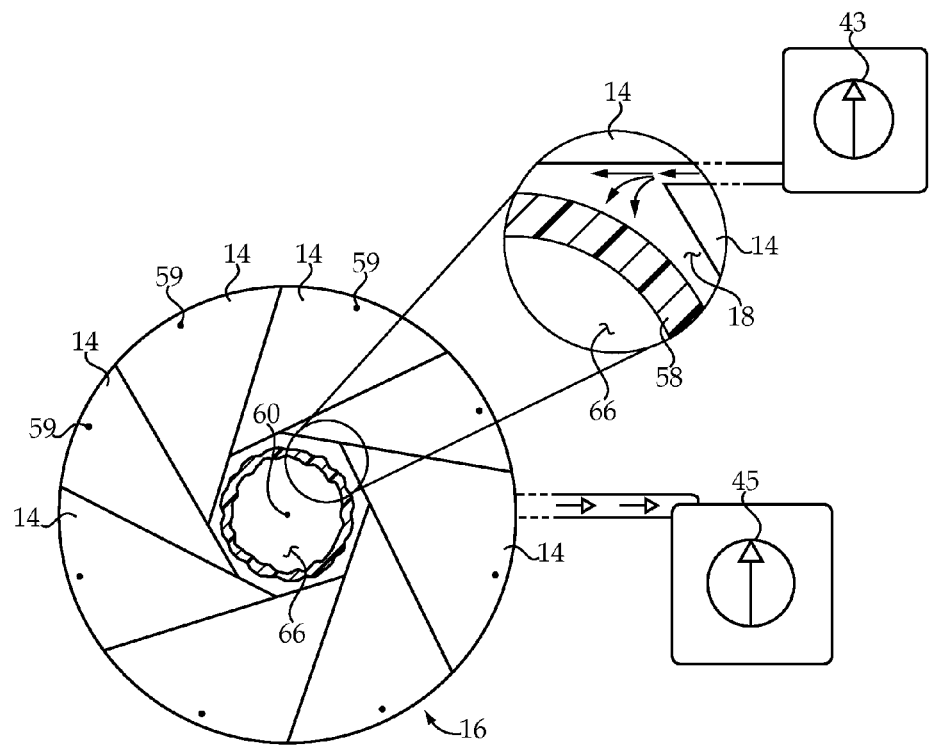
FIG. 6 is an axial view, partially sectioned, through a portion of a molding system, at another stage of a blow molding procedure.

Referring also now to FIG. 6, there is shown elongate body 50 in a view similar to that of FIG. 5, and illustrating in a detailed enlargement where pump 43 has been used to supply cooling air into housing 12, such that the cooling air passes between blade members 14 and about tubular wall 58 to hasten cooling of material forming elongate body 50. Also shown in FIG. 6 is pump 45 having been reversed in direction so as to apply a negative pressure to lumen 66 to inwardly deform tubular wall 58 to increase a flow area for the cooling fluid. In FIGS. 5 and 6 pivot axes 59 for each of movable blade members 14 are also shown.

In certain embodiments, movable blade members 14 will be maintained at fixed positions during the blow molding process, hence they will not be adjusted about axes 59 during any individual molding cycle. In other embodiments, movable blade members 14 might be adjusted to change a size of iris 16 during the blow molding of an individual balloon in an elongate body. For instance, in one example embodiment, as the tubular wall expands outwardly in response to increased fluid pressure blade members 14 might be pivoted about their pivot axes 59 to increase a size of cavity 18. The increasing in size could occur continuously, or in a step-wise manner. In other instances, movable blade members 14 might be maintained at fixed positions until just prior to the point at which cooling air begins to be pumped between them and about the balloon to hasten its cooling. At that point, movable blade members 14 might be pivoted to enlarge iris 18, and assist in the creation of flow space for cooling air. Those skilled in the art will envision still further variations that might be obtained by way of the flexibility to adjust the size of iris 18.

Figure 8:
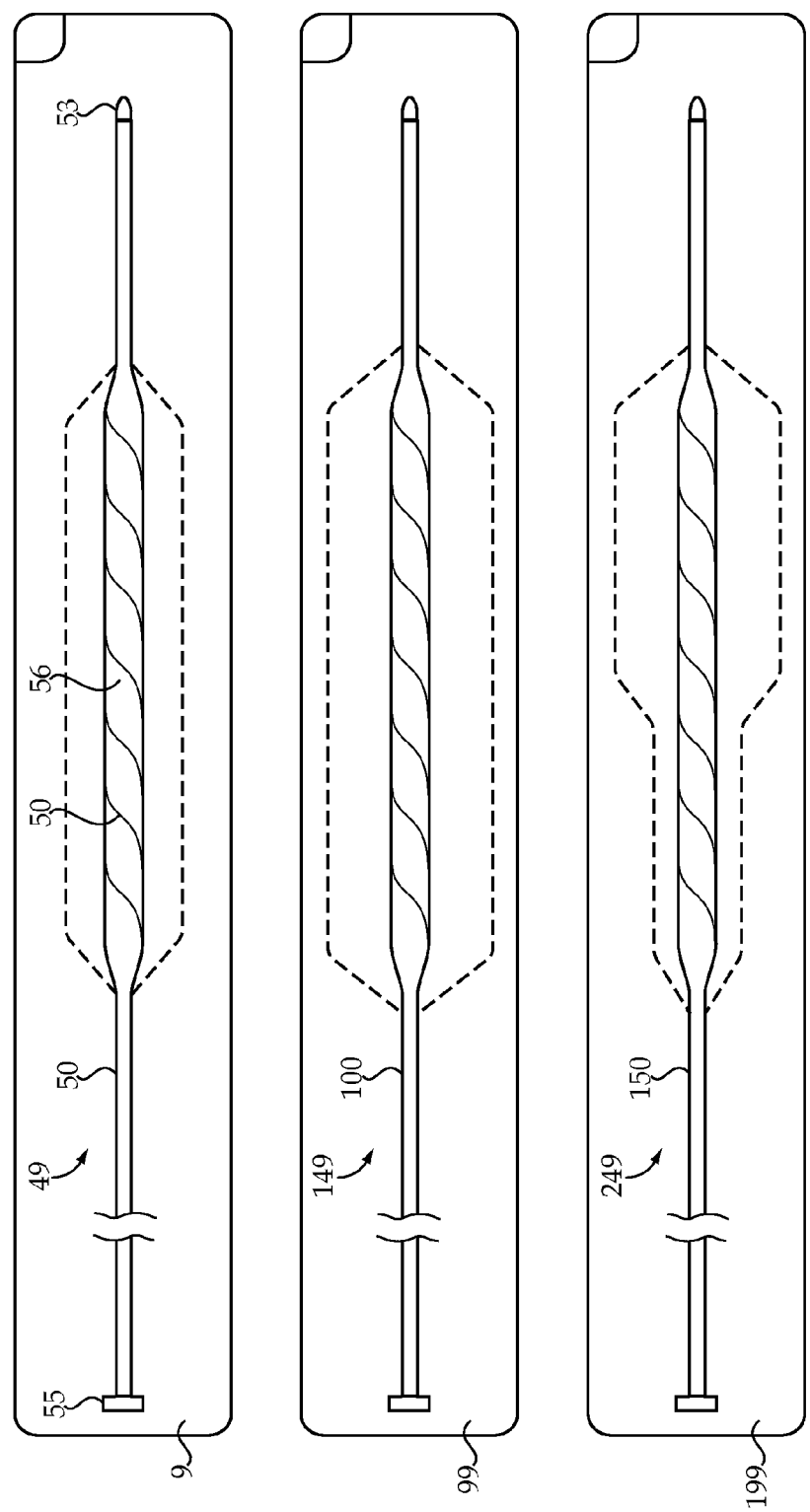
FIG. 8 is a side diagrammatic view of an inventory of balloon catheters, according to one embodiment.

Referring now to the drawings generally, but in particular now to FIG. 7a, there is shown an example series of processing steps used in producing an inventory of balloon catheters according to the present disclosure. It will be appreciated that the present description of FIG. 7a, and also FIGS. 7b, 7c and FIG. 8, are applicable to any of the tubular bodies, molding systems, and other apparatus and techniques discussed herein. Similarly, features of the blow molding process described above such as heating, increasing of fluid pressure, application of negative pressure, the use of cooling air, for instance, can all be applied to the production of a balloon catheter inventory as illustrated in FIGS. 7a-c.

In FIG. 7a, elongate body 50 is first shown to the left as it might appear prior to being advanced into cavity 118 formed by iris 116 in system 110 at a mold stage of processing. Elongate body 50 is processed in system 110 so as to blow mold a first balloon therein while molding iris 116 is held in a first state determining a configuration of the first balloon. From the mold stage, elongate body 50, with a balloon now formed therein can be advanced to a fold stage, in a known folding or balloon pleating machine 210, and thenceforth to an assembly stage where a proximal fitting and a distal tip are attached to the elongate body with the now folded balloon to form a balloon catheter. From the assembly stage in FIG. 7a, the elongate body may be advanced to a sterilize and package stage where it is placed within sterile, peel open package 99.

Referring now to FIG. 7b, there is shown another elongate body 100 as it might appear just prior to being advanced into cavity 118 in place of first elongate 50. Second elongate body 100 may be processed so as to blow mold a balloon therein while molding iris 116 is held in a second state determining a configuration of the second balloon. From the mold stage in FIG. 7b, elongate body 100 may be forwarded to the fold stage, the assembly stage, and incorporated in a balloon catheter 149 placed within a sterile peel open package 99. Referring to FIG. 7c, there is shown yet another elongate body 150 as it might appear ready to be advanced into cavity 118 with molding iris 116 in yet another configuration, this time with multiple different diameters. Elongate body 150 may be molded in molding system 110, and then advanced to a fold stage, an assembly stage, and a sterilize and package stage where it is incorporated into a balloon catheter 249 placed in a sterile, peel open package 199.

From the foregoing description, it will be understood that each of FIGS. 7a, 7b and 7c may represent a production run where a balloon catheter having different characteristics is made. It will further be appreciated that many balloon catheters might be made according to the processing steps as set forth in each of FIGS. 7a, 7b and 7c. Between the production runs, or potentially during the production runs, iris 116 can be adjusted via moving movable blade members 14. Accordingly, after a plurality of elongate bodies similar to elongate body 50 are blow molded, system 110 may be adjusted and a plurality of elongate bodies similar to 100 formed, and so on. Between the production runs, the internal diameter of cavity 118 is adjusted, either throughout the cavity as evident from the difference between FIGS. 7*a* and 7*b*, or within the cavity as depicted in FIG. 7*c*. In the case of adjusting the internal diameter of molding iris 116 between blow molding a balloon in elongate body 50 and blow molding a balloon in elongate body 100, the movable blade members may be moved so as to change the internal diameter of molding iris 116 uniformly. Where adjusting between blow molding a balloon in elongate body 100 and a balloon in elongate body 150, the blade members may be adjusted so as to change the internal diameter of molding iris 116 to different relative extents at different axial locations.

Referring also now to FIG. 8, there is shown an inventory of balloon catheters, including one catheter of each of the general kinds shown processed in FIGS. 7*a-c*. Tip 53 has been affixed to elongate body 50, as has been a fitting 55. A plurality of pleats 51 are evident in the now folded balloon formed by middle segment 56. Similar features and components are found in balloon catheters 149 and 249. It is contemplated that the present disclosure will provide efficiency improvements over prior strategies for producing an inventory of balloon catheters. Rather than switching between molding dies, the balloon molding iris itself can be adjusted. Changeover in iris size or configuration between production runs, or even adjustments during a production run, can be executed quite rapidly. Moreover, in a manner discussed above the capability of adjustments to the molding iris provides new opportunities for molding process development not possible with fixed size dies.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will apparent upon an examination of the attached drawings and appended claims.

What is claimed is:

1. A method of making a balloon catheter comprising the steps of:
    moving a plurality of blade members defining a cavity in a molding iris so as to adjust the molding iris from a first state to a second state;
    advancing an elongate body into the cavity;
    increasing a temperature of material forming the elongate body so as to soften the material, once positioned within the cavity;
    increasing a fluid pressure within a lumen extending longitudinally through the elongate body;
    plastically deforming a segment of the elongate body formed by the softened material, in response to the increased fluid pressure, so as to outwardly expand the segment; and
    limiting the outward expansion via contacting the segment with the plurality of movable blade members, such that upon hardening of the material the segment forms an inflatable balloon having a configuration determined by the second state of the molding iris and in fluid communication with the lumen in an adjoining segment of the tubular body.

2. The method of claim 1 wherein the step of moving further includes moving the plurality of blade members so as to change an internal diameter of the cavity.

3. The method of claim 2 wherein the molding iris defines a longitudinal center axis, and wherein the step of moving further includes moving the plurality of blade members so as to change the internal diameter of the molding iris to a different relative extent at different axial locations.

* * * * *